United States Patent [19]

Davis, Jr.

[11] 4,240,028
[45] Dec. 16, 1980

[54] MEANS AND METHOD FOR DETERMINING WATER SATURATION OF OIL

[75] Inventor: Lorne A. Davis, Jr., Houston, Tex.

[73] Assignee: Texaco Inc., White Plains, N.Y.

[21] Appl. No.: 33,937

[22] Filed: Apr. 27, 1979

[51] Int. Cl.[3] .......................................... G01R 27/26
[52] U.S. Cl. .................................... 324/61 R; 73/73; 324/61 QS
[58] Field of Search ................. 324/61 R, 61 P, 60 C, 324/61 QS, 61 QL; 73/73; 364/556; 340/200

[56] References Cited

U.S. PATENT DOCUMENTS

| | | | |
|---|---|---|---|
| 2,772,393 | 11/1965 | Davis | 324/61 QS |
| 3,979,581 | 9/1976 | Reuland | 324/61 R |
| 4,044,607 | 8/1977 | Deal | 73/73 |

*Primary Examiner*—Ernest F. Karlsen
*Attorney, Agent, or Firm*—Carl G. Ries; Robert A. Kulason; Ronald G. Gillespie

[57] ABSTRACT

Apparatus, for determining water saturation of a fluid in a core sample or flowing in a pipe, includes a sensor spacially arranged with the pipe or the core sample providing a signal whose frequency and amplitude corresponds to the water saturation. A circuit connected to the sensing means provides a difference signal corresponding to the voltage difference between the signal from the sensor and a reference level established for the signal from the sensor corresponding to substantially 100% water saturation. A local oscillator provides a local signal whose frequency corresponds to a substantially 100% water saturation condition. A mixer connected to the sensor and to the local oscillator provides a signal having a frequency that corresponds to the difference between the frequencies of the signals from the sensor and the local oscillator. A frequency to voltage converter connected to the mixer provides a signal whose amplitude corresponds to the frequency of the mixer's signal. A network provides a signal corresponding to the water saturation in accordance with the signals from the circuit and the converter.

8 Claims, 2 Drawing Figures 4,240,028

MEANS AND METHOD FOR DETERMINING WATER SATURATION OF OIL

BACKGROUND OF THE INVENTION

Field of the Invention

The present invention relates to monitors and monitoring methods in general and, more particularly, to monitors and monitoring methods for determining water saturation in oil.

SUMMARY OF THE INVENTION

Apparatus for determining the water saturation of a fluid in a core sample or flowing in a pipe includes a sensor, spatially arranged with the pipe or the core sample, which provides a signal whose frequency and amplitude corresponds to the water saturation. A circuit connected to the sensor provides a difference signal corresponding to the voltage difference between the signal from the sensor and a reference level, established for the sensor's signal, for substantial 100% water saturation. A local oscillator provides a local signal whose frequency corresponds to a substantially 100% water saturation condition. A mixer connected to the sensor and to the local oscillator provides a signal having a frequency that corresponds to the difference between the frequencies of the sensor's signal and the oscillator's signal. A frequency to voltage converter provides a signal whose amplitude corresponds to the mixer's signal frequency. A network provides an output, corresponding to the water saturation, in accordance with signals from the circuit and the converter.

The objects and advantages of the invention will appear more fully hereinafter from a consideration of the detailed description which follows, taken together with the accompanying drawings, wherein one embodiment of the invention is illustrated by way of example. It is to be expressly understood, however, that the drawings are for illustration purposes only, and are not to be construed as defining the limits of the invention.

DESCRIPTION OF THE INVENTION

Figure 1:
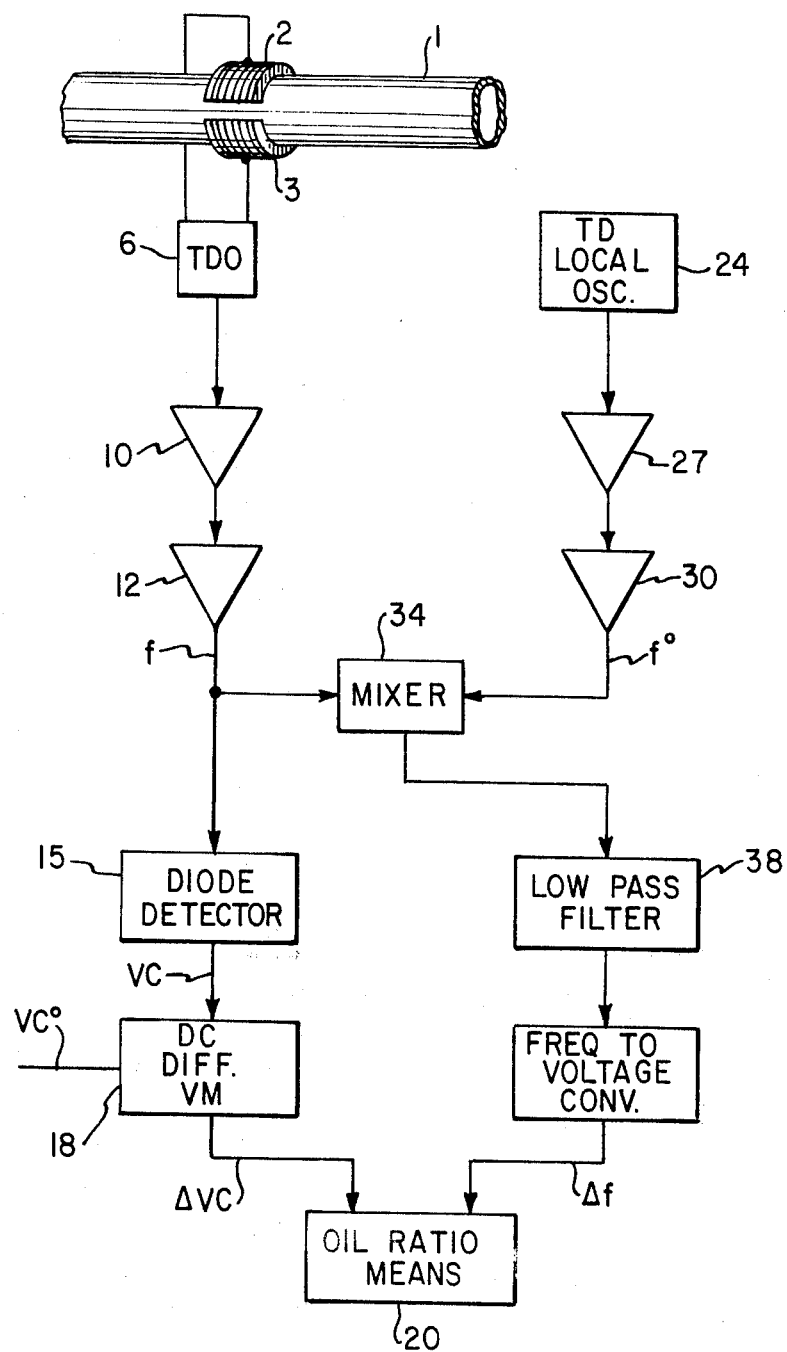
FIG. 1 is a simplified block diagram of a water saturation monitor constructed in accordance with the present invention.

Referring to FIG. 1, a non-conducting pipe 1 carrying crude oil or a mixture of oil and water has capacitor plates 2 and 3 attached to it. It should be noted that plates 2 and 3 could also be used with a core sample from a well traversing an earth formation to measure water saturation. A tunnel diode oscillator 6 is electrically connected to plates 2 and 3 and provides a signal whose frequency corresponds to the liquid mixture flowing in pipe 1. A buffer amplifier 10 receives the signal from oscillator 6 and provides it to an amplifier 12 which in turn provides signal f whose frequency corresponds to the liquid mixture.

Signal f is applied to a diode detector 15 which provides a corresponding DC signal VC differential voltmeter 18. Voltmeter 18 is initially adjusted, as indicated by the line marked VC°, to a null setting, with only water in pipe 1. Voltmeter 18 provides a signal ΔVC corresponding to the voltage difference between signal VC, corresponding to the mixture being examined, and the null setting VC° for water. Signal ΔVC is provided to oil ratio means 20.

A tunnel diode local oscillator 24 has its tuning capacitor located internally. Oscillator 24 is adjusted, as hereinafter explained, to provide a signal to a buffer amplifier 27 which in turn provides the signal to an amplifier 30. Amplifier 30 provides a signal f° to a mixer 34 also receiving signal f. Mixer 34 provides a signal that corresponds to the difference between f and f°.

Initially, the tuning capacitor in oscillator 24 is adjusted when there is only water in pipe 1 so that mixer 34 provides a zero output. This adjustment establishes the frequency of the signal from oscillator 24 and hence the frequency of f°.

Mixer 34 provides a signal to a low pass filter 38 which in turn provides a corresponding signal to a frequency to voltage converter 40. Converter 40 provides a voltage Δf, corresponding to the frequency difference between signals f and f°, to oil ratio means 20.

Figure 2:
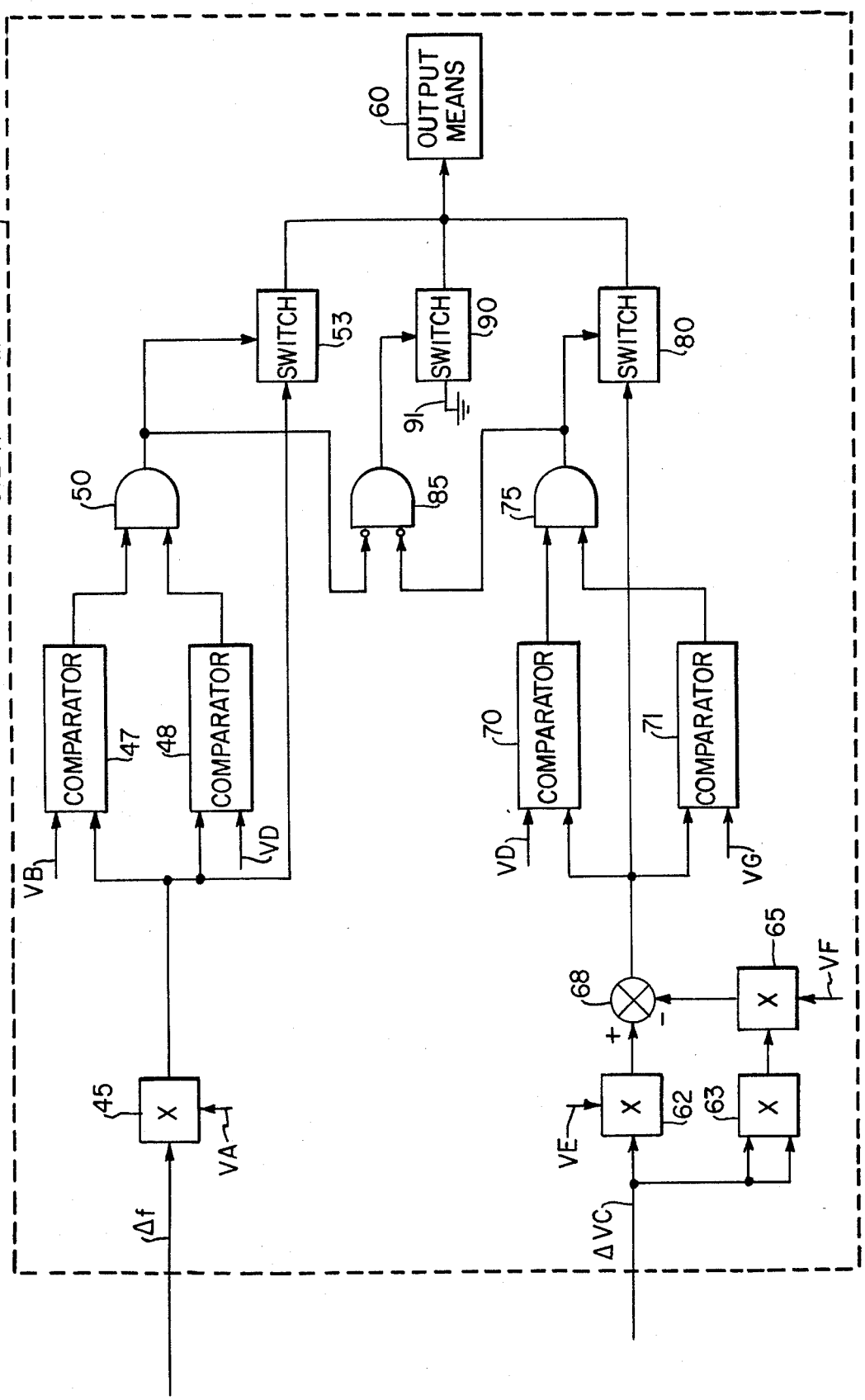
FIG. 2 is a detailed block diagram of the oil ratio means shown in FIG. 1.

Referring now to FIG. 2, oil ratio means 20 includes a multiplier 45 multiplying signal f with a DC voltage VA corresponding to a factor having a preferred value of 0.478. Multiplier 45 provides a product signal to comparators 47, 48, receiving reference voltages VB and VD, respectively, corresponding to values of 1.0 and 0.5, respectively. Comparators 47, 48 provide their outputs to an AND gate 50. Comparators 47, 48 provide high logic level outputs when the amplitude of the signal from multiplier 45 is within the limits defined by reference voltages VB and VD, i.e. the product (VA)(Δf) is within a range of 0.5 to 1.0. The high logic level outputs cause AND gate 50 to provide an output, at a high logic level, to an electronic switch 53, receiving the signal from multiplier 45. Switch 53 passes the signal from multiplier 45 to output means 60 when AND gate 50 provides a high logic level output and blocks the signal when AND gate 50 output is at a low logic level.

When the product signal from multiplier 45 is greater than voltage VB, comparator 47 output goes to a low logic level. When the product signal from multiplier 45 is less than reference voltage VD, comparator 48 provides a low logic level output. When either comparator 47 or 48 provides a low logic level output, AND gate 50 provides a low logic level output.

Signal ΔVC is provided to multipliers 62, 63. Multiplier 62 multiplies signal ΔVC with a DC voltage VE, corresponding to a factor having a preferred value of 1.71, to provide a product signal. Multiplier 63 effectively squares and provides a corresponding signal to another multiplier 65 where it is multiplied with a DC voltage VF, corresponding to a factor having a preferred value of 0.0147. Subtracting means 68 subtracts the signal provided by multiplier 65 from the signal provided by multiplier 62 to provide a signal to comparators 70, 71.

Comparator 70 compares the signal from subtracting means 68 with reference voltage VD and provides an output at a high logic level when the signal from subtracting means 68 is equal to or less than voltage VD and at a low logic level when the signal is greater than voltage VD. Comparator 71 compares the signal from subtracting means 68 with a DC reference voltage VG, corresponding to a value of 0.1, and provides an output at a high logic level when the signal is equal to or greater than voltage VG and at a low logic level when the signal is less than voltage VG.

An AND gate 75 is connected to comparators 70, 71 and provides an output at a high logic level when the outputs from comparators 70, 71 is at a high logic level and at a low logic level when one or both outputs from comparators 70, 71 are at a low logic level. An electronic switch 80, whose output is connected to the output of switch 53, is controlled by the output from AND gate 75 to pass the signal from subtracting means 68 to output means 60 when AND gate 75 output is at a high logic level and to block the signal from subtracting means 68 when AND gate 75 output is at a low logic level.

An AND gate 85 has two inverting inputs connected to AND gates 50, 75 so that when either comparator 50 or 75 provides a high logic level output, AND gate 85 provides a low logic level output. When comparators 50, 75 both provide low logic level outputs, AND gate 85 provides a high logic level output. Switch 90 is connected to ground 91 and an output connected to the outputs of switches 53, 80 and hence to output means 60. Switch 90 effectively grounds the input to output means 60 when neither signal $\Delta f$ (as modified) or signal $\Delta VC$ (as modified) is within the proper limits and does not ground the input to output means 60 when either switch 53 or switch 80 is providing a signal to output means 60.

Output means 60 may either record or display, or both, the water saturation of the mixture in pipe 1 or of the core sample in accordance with the signal applied to its input.

The present invention as hereinbefore described tests a liquid mixture in a pipeline or a core sample of an earth formation for water saturation.

What is claimed is:

1. Apparatus for determining the water saturation of a fluid flowing in a pipe or of a core sample, comprising sensing means spatially arranged with the fluid or core sample for providing a signal whose amplitude and frequency corresponds to the water saturation, difference means connected to the sensing means for providing a difference signal corresponding to the voltage difference between the signal from the sensing means and a reference level established for the signal from the sensing means for substantial 100% water saturation, local oscillator means for providing a local signal whose frequency corresponds to a substantially 100% water saturation condition, mixer means connected to the sensing means and to the local oscillator means for providing a signal having a frequency that corresponds to the difference between the frequencies of the signals from the sensing means and the local oscillator means, converter means connected to the mixer means for providing a DC voltage whose amplitude corresponds to the frequency of the mixer means signal, and oil ratio means connected to the difference means and to the converter means for providing an output corresponding to the water saturation of the fluid or core sample in accordance with the signals from the difference means and the converter means.

2. Apparatus as described in claim 1 in which the sensing means includes a tunnel diode oscillator having capacitor plates arranged so that the fluid or core sample is between said plates so that the tunnel diode oscillator provides a signal whose frequency and amplitude varies in accordance with the composition of the fluid in the pipe or in the core sample, and amplifier means connected to the tunnel diode oscillator for amplifying the signal from the tunnel diode oscillator to provide a signal f.

3. Apparatus as described in claim 2 in which the difference means includes a diode detector connected to the first amplifier means for providing a voltage VC in accordance with the signal f, and a DC differential voltmeter connected to the diode detector means and calibrated so as to provide a voltage output $\Delta VC$ corresponding to the difference between voltage VC and a voltage level VCO, corresponding to substantially 100% water flowing in the pipe or in the sample.

4. Apparatus as described in claim 3 in which the local oscillator means includes a tunnel diode local oscillator providing a signal whose frequency corresponds to a substantially 100% water saturation condition, and second amplifier means connected to the tunnel diode local oscillator for amplifying the signal therefrom and providing it as signal $f^o$.

5. Apparatus as described in claim 4 in which the oil ratio means includes first multiplier means receiving signal $\Delta f$ and a DC voltage VA for multiplying the received signal and voltage to provide a product signal, first control means receiving the product signal from the first multiplier means for providing a control signal at one level when the product signal is within first predetermined reference limits and providing the control signal at another level when the product signal is not within the first predetermined limits, second multiplying means receiving signal $\Delta VC$ and a DC voltage VE for multiplying the received signal and voltage to provide a product signal, a third multiplier means receiving signal $\Delta VC$ for providing a signal corresponding to the square of $\Delta VC$, a fourth multiplier means connected to the third multiplying means for multiplying the signal from the third multiplying means with the direct current voltage VF, subtracting means for subtracting the signal provided by the fourth multiplying means from the signal provided by the third multiplying means to provide a corresponding signal, second control means connected to the subtracting means for providing a second control signal at one level when the signal from the subtracting means is within second predetermined limits and providing a second control signal at another level when the signal from the subtracting means is not within the second predetermined limits, third control means connected to the first and second control means for providing a third control signal at one amplitude when the first and second control signals are at the other amplitudes, and for providing the third control signal at the other amplitude when at least one of the control signals of the first and second control signals is at the one amplitude, first switching means connected to the first multiplying means and to the first control means for passing the signal from the first multiplying means when the first control signal is at the one amplitude and for blocking the signal from the first multiplying means when the first control signal is at the other amplitude, second switching means connected to the subtracting means and to the second control means for passing the signal from the subtracting means when the second control signal is at the one amplitude and for blocking the signal from the subtracting means when the second control signal is at the other amplitude, third switching means connected to the third control means and to ground for providing a substantially zero output when the third control signal is at the one ampitude and for not providing a substantially zero output when the third control signal is at the other amplitude, and output network means having an input connected to the three switching means for providing the output in accordance with the signals passed by the three switching means.

6. Apparatus as described in claim 5 in which the first control means includes a first comparator connected to the first multiplying means and receiving a direct current voltage VB corresponding to one reference limit for the signal from the multiplying means and providing a signal at one amplitude when the signal from the first multiplying means is equal to or less than voltage VB and at another amplitude when the signal from the first multiplying means is greater than voltage VB, second comparator means connected to the first multiplying means and receiving a DC voltage VD corresponding to another limit for the signal from the first multiplying means for providing a signal at the one amplitude when the signal from the first multiplying means is equal to or greater than voltage VD and at another amplitude when the signal from the first multiplying means is less than the voltage VD, and a first AND gate connected to the two comparator means and to the first switching means for providing the first control signal at the one amplitude when the signals from the comparator means are at the one amplitude and for providing the control signal at the other amplitude when at least one of the signals from the comparator means is at the other amplitude.

7. Apparatus as described in claim 6 in which the second control means includes third comparator means receiving the signal from subtracting means and voltage VD for providing a signal at one amplitude when the signal from the subtracting means is equal to or less than voltage VD and at another amplitude when the signal from the subtracting means is greater than voltage VD, fourth comparator means connected to the subtracting means and receiving a DC voltage VG for providing a signal at one amplitude when the signal from the subtracting means is equal to or greater than the voltage VG and at another amplitude when the signal from the subtracting means is less than the voltage VG, and second AND gate means connected to the third and fourth comparator means for providing the second control signal at the one amplitude when the signals from the third and fourth comparator means are at the one amplitude and for providing the second control signal at the other amplitude when one of the signals of the signals from the third and fourth comparator means is at the other amplitude.

8. A method for determining the water saturation of a fluid flowing in a pipe or of a core sample, comprising the steps of sensing, with a sensor spacially arranged with the fluid or core sample, the water saturation; providing a sensed signal whose amplitude and frequency corresponds to the water saturation; providing a first difference signal corresponding to the voltage difference between the sensed signal and a reference level established for the sensed signal for substantial 100% water saturation; providing a local signal whose frequency corresponds to a substantially 100% water saturation condition; providing a second difference signal having a frequency that corresponds to the difference between the frequencies of the sensed signal and the local signal; providing a DC voltage whose amplitude corresponds to the frequency of the second difference signal; and providing an output corresponding to the water saturation of the fluid or core sample in accordance with the DC voltage and the difference signal.

* * * * *